United States Patent [19]

Bowers et al.

[11] Patent Number: 5,733,449
[45] Date of Patent: Mar. 31, 1998

[54] MICROCONCENTRATOR DEVICE

[75] Inventors: William F. Bowers, Topsfield; Basil Yankopoulos, Peabody, both of Mass.

[73] Assignee: Orbital Biosciences, LLC, Topsfield, Mass.

[21] Appl. No.: 569,855

[22] Filed: Dec. 8, 1995

[51] Int. Cl.$^6$ .................................................. B01D 63/00
[52] U.S. Cl. ............................ 210/321.6; 210/360.1; 210/369; 210/380.1; 210/321.75; 210/455; 422/101
[58] Field of Search ............................ 210/477, 321.75, 210/321.84, 380.1, 360.1, 455, 450, 369, 321.6; 422/100, 101

[56] References Cited

U.S. PATENT DOCUMENTS

| | | | |
|---|---|---|---|
| 3,356,219 | 12/1967 | Müller | 210/193 |
| 3,386,585 | 6/1968 | Weyand et al. | 210/445 |
| 3,471,019 | 10/1969 | Trasen et al. | 210/94 |
| 3,481,477 | 12/1969 | Farr | 210/359 |
| 3,488,768 | 1/1970 | Rigopulos | . |
| 3,512,940 | 5/1970 | Shapiro | . |
| 3,583,627 | 6/1971 | Wilson | . |
| 3,608,736 | 9/1971 | Wong | 210/477 |
| 3,682,321 | 8/1972 | Smith | 210/477 |
| 3,693,804 | 9/1972 | Grover | 210/359 |
| 3,701,434 | 10/1972 | Moore | 210/477 |
| 3,817,379 | 6/1974 | Zipilivan et al. | 210/94 |
| 3,832,141 | 8/1974 | Haldopoulos | 23/259 |
| 4,017,396 | 4/1977 | Skau | 210/232 |
| 4,066,512 | 1/1978 | Lai et al. | 195/127 |
| 4,162,979 | 7/1979 | Wahlefeld et al. | 210/282 |
| 4,614,585 | 9/1986 | Mehra et al. | 210/455 |
| 4,632,761 | 12/1986 | Bowers et al. | 210/650 |
| 4,755,301 | 7/1988 | Bowers et al. | 210/650 |
| 4,769,145 | 9/1988 | Nakajima | 210/455 |
| 4,832,851 | 5/1989 | Bowers et al. | 210/650 |
| 5,112,484 | 5/1992 | Zuk, Jr. | 210/247 |
| 5,308,483 | 5/1994 | Sklar et al. | 210/455 |
| 5,443,723 | 8/1995 | Stankowski et al. | 210/321.75 |

OTHER PUBLICATIONS

Filtron Microsep® Catalog (1993), pp. 1–5.
Amicon "Membrane Filtration Chromatography" Catalog (1993), cover and pp. 17 & 21.

*Primary Examiner*—Ana Fortuna
*Attorney, Agent, or Firm*—Nutter, McClennen & Fish, LLP

[57] ABSTRACT

A reusable microconcentrator device may be disassembled, cleaned and reassembled before use. The microconcentrator device of the invention is typically useful in filtering and separating small samples of solutions and suspensions. The microconcentrator device of the invention includes an elongate sample sleeve, a base element which can be removable and replaceably coupled to a centrifugal portion of the sleeve, a compliant membrane compressing feature, and a disposable membrane. Preferably, the base element includes an O-ring which compresses the membrane to seal it to the centrifugal surface of an annular ledge portion of the sleeve, which also forms a deadstop. Among the advantages of the microconcentrator device of the invention is that a reliable retentate volume remains following filtration. The elements of the microcentrator device can also be permanently assembled to one another.

29 Claims, 10 Drawing Sheets

MICROCONCENTRATOR DEVICE

BACKGROUND OF THE INVENTION

The invention relates to a centrifugal filtration device for separating and concentrating macromolecules or particles, such as viruses, from a solution or suspension. More particularly, the invention relates to centrifugal ultrafiltration devices that protect against filtration to dryness.

Many chemical and biochemical techniques require separation of macromolecules or particles from a solution or suspension. Many such techniques involve the removal of buffer and salts from a protein solution to yield a highly concentrated protein sample that is to be further analyzed or utilized.

A technique commonly used for concentrating such solutions is centrifugal ultrafiltration. One problem that is inherent to the process of subjecting samples of a solution or suspension to centrifugal ultrafiltration techniques is the potential that the sample will be filtered to dryness. Filtration to dryness can reduce the biological activity of any retained macrosolute (e.g., protein) and can also reduce the total mass recovery of macromolecules. Attempts to re-dissolve the retained macrosolute after filtration to dryness, by adding a buffer, are not always effective to overcome the reduced biological activity or the reduced recovery. It is most effective to cease filtration once a desired final retentate volume is achieved.

This end is well served by the "deadstop" means of the microconcentrator taught by Bowers and Rigopulos in U.S. Pat. No. 4,632,761. This deadstop means is a hydrostatic barrier created by the membrane support base which has filtrate duct or ducts offset inward from the edge of the wall of the sample sleeve. When used in a fixed angle centrifuge rotor and the retentate meniscus reaches the centrifugal radial level of the outermost edge of the outermost filtrate duct, filtration stops due to the counterbalancing hydrostatic pressure of filtrate contained between the remaining wetted membrane area and the membrane support base. This design has the significant advantage of offering maximal available membrane surface area and resulting filtration rate for a given size flat membrane disk fitting into a given device tube diameter.

An alternative known deadstop means is to provide an impermeable cover or coating to a portion of the membrane area. U.S. Pat. No. 3,817,379 describes an impermeable coating on a portion of the membrane in the bottom of an adsorbent-driven concentrator. This coating only partially impedes filtration, due to the wicking by surface tension seen at ambient gravity, which allows continued slower filtration after the meniscus reaches the coated portion of the membrane. Several known centrifugal concentrators now provide a plastic molded deadstop ledge as part of the retentate chamber. Centrifugal devices have the advantage that wicking is eliminated due to the higher gravitational field of the centrifuge. However, the membrane area covered by the deadstop ledge is unavailable for filtration, which results in a lower filtration rate, compared to the same size membrane contained in a device with a hydrostatic deadstop.

The hydrostatic deadstop design of U.S. Pat. No. 4,632,761 offers the additional benefit of membrane seal reliability. Because the deadstop means is beneath the membrane, in larger volume devices a conventional O-ring may be used above the membrane to form a seal between the delicate solute-rejecting top skin of the ultrafiltration membrane and the outer edge of the retentate sleeve, to prevent some volume of the concentrated macrosolute from being lost by seeping through the perimeter seal into the filtrate tube. The compliant O-ring elastomer provides a uniform crushing of the porous membrane, and easily corrects for small differences in membrane thickness or dimensions of the retentate sleeve and membrane support.

With impermeable deadstop centrifugal microconcentrators, and even for hydrostatic deadstop devices of smaller device sizes, it is not practical to use an O-ring to form the seal between the membrane top skin and the retentate sleeve. The axial thickness of the O-ring occupies the volume just above the membrane needed for retentate storage with an impermeable deadstop. Furthermore, in smaller devices, the radial thickness of the ring becomes too large a fraction of the total disk area, resulting in unacceptably slow filtration rates. Another objection to O-rings used as seals above the membrane has been the potential for contamination of macrosolute retentate by oils added to many elastomer formulations as processing aids.

These factors have led to designs for smaller volume microconcentrators which seal the ultrafiltration membrane by simply squeezing it between the retentate sleeve and the membrane support. Variations in membrane thickness, in molded sleeve and membrane support dimensions, and in assembly processing make consistent reliable crush sealing quite challenging, and seal leakage has been a significant ongoing problem with many noncompliant crush-sealing designs.

Currently available centrifugal microconcentrator devices, which are designed to concentrate volumes of a few milliliters or less, are all manufactured as preassembled disposable integral units. These devices can, at best, be reused only a few times by washing out remaining retentate product to minimize carryover between samples. The need to use disposable microconcentrator devices for centrifugal filtration applications can add significantly to the cost of basic research and other procedures that require separation and concentration of macromolecules and other suspended solids from small volumes of liquids.

Accordingly, an object of the present invention is to provide a microconcentrator device for use in centrifugal ultrafiltration applications that avoids the problems associated with filtering to dryness by yielding a reliable fixed volume of retentate. A further object of the invention is to provide a compliant microconcentrator device that has good sealing properties so as to prevent the seepage of unfiltered sample into the filtrate cup. It is also an object of the invention to prevent contamination of macrosolute retentate by oils from an elastomeric seal. Another object of the invention is to provide a reusable microconcentrator device that can be simply and reliably assembled, disassembled and reassembled by the user with fresh membranes of a variety of different pore sizes. Yet another object of the invention is to maximize the available membrane surface area, consistent with other objects. These and other objects will be apparent to one of ordinary skill in the art upon reading the disclosure that follows.

SUMMARY OF THE INVENTION

The invention provides a microconcentrator device for use in centrifugal ultrafiltration applications. Among the advantages of the microconcentrator device of the invention is that the microconcentrator device provides a reliable retentate volume, thus eliminating problems associated with filtering to dryness. Further, in one embodiment the microconcentrator device is reusable and may be easily disassembled, cleaned and reassembled by the user with a fresh membrane.

The microconcentrator device of the invention is useful for separating and concentrating macromolecules or particles from a solution or a suspension. The microconcentrator device of the invention fits within a filtrate collection tube that has a closed centrifugal end and an open centripetal end. The microconcentrator device comprises an elongate sleeve that is matable into the filtrate collection tube. The sleeve is of a substantially cylindrical shape and has openings at centripetal and centrifugal ends thereof. Further, the elongate sleeve includes an annular ledge disposed at a centrifugal portion of the sleeve. A base element can be removably mountable upon the centrifugal end of the sleeve, adjacent to the centrifugal side of the ledge. The base element has a centripetal surface and a centrifugal surface with one or more apertures or flow ports extending therethrough. The device also includes a coupling arrangement that succeeds in securely mounting the base element to a centrifugal end of the sleeve such that the base element is joined to the sleeve while abutting the centrifugal side of the annular ledge. The base element must be coupled to the sleeve in a manner that prevents seepage of unfiltered sample.

In one embodiment, a removable membrane is adapted to be placed between the centripetal surface of the removable base and the centrifugal surface of the annular ledge. This embodiment envisions the mounting of a gasket on the centripetal surface of the base element in contact with the centrifugal (inactive) surface of the membrane to enhance sealing characteristics.

In one embodiment the centripetal surface of the base element has a plurality of concentric, raised circular ridges with the apertures or flow channels disposed between the ridges. Alternatively, the centripetal surface of the base element has a convex cross section and flow channels in the surface of the base element are formed within one or more stepped shoulders.

The microconcentrator device of the invention may also exist in the form of a disposable embodiment in which the elements noted above are substantially permanently assembled. In this embodiment the device cannot normally be disassembled and reassembled.

DETAILED DESCRIPTION OF THE INVENTION

Figure 1:
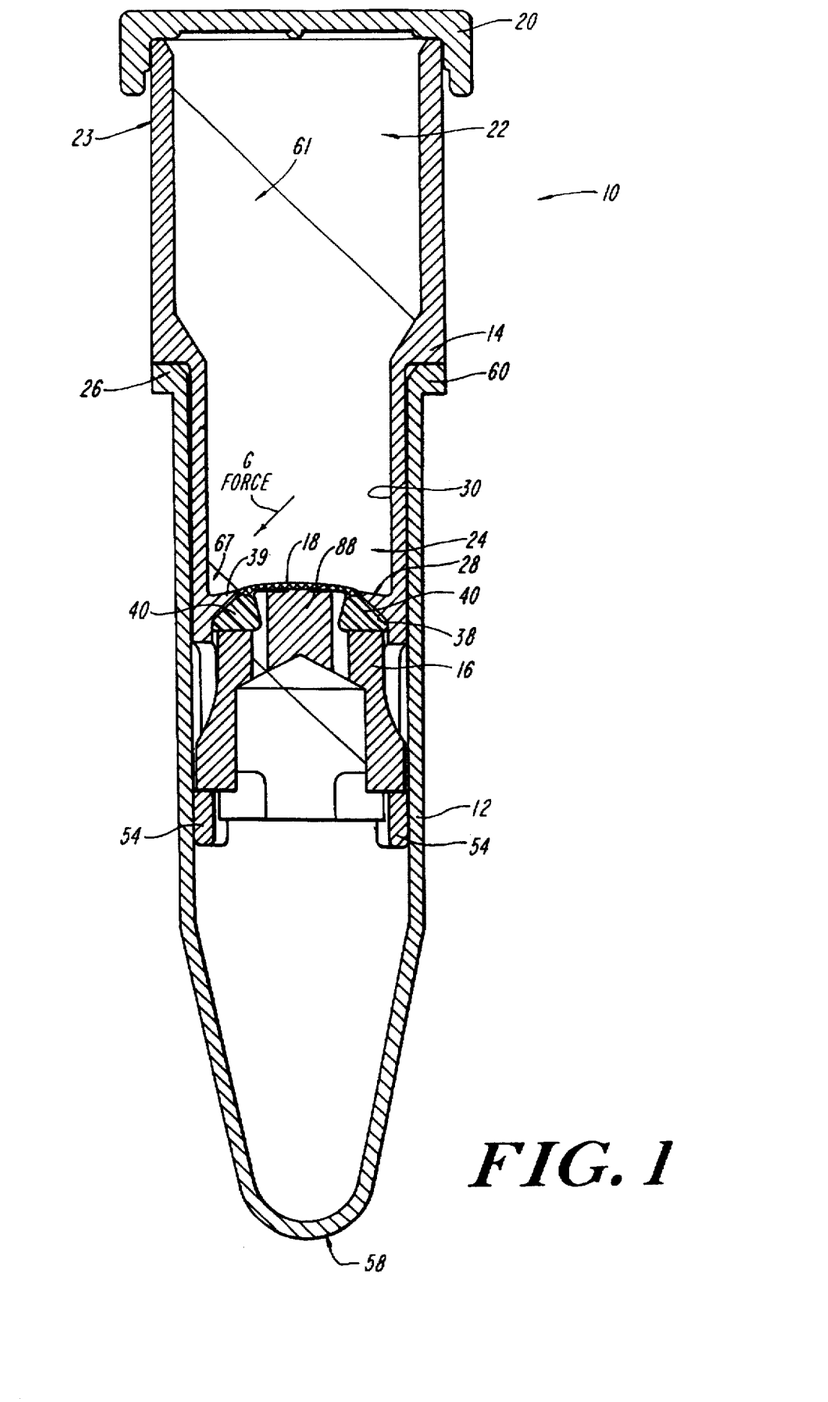
FIG. 1 is a side, sectional view of the microconcentrator device of the present invention, including a filtrate collection tube.
Figure 2:
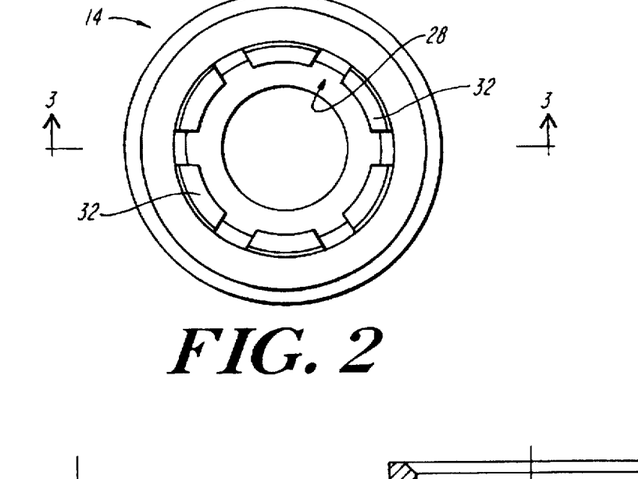
FIG. 2 is a bottom view of a sample receiving sleeve that forms part of one embodiment of the microconcentrator device of the invention.

As illustrated in FIG. 1, microconcentrator device 10 includes a sample sleeve 14, a removable base element 16, an O-ring or gasket 40, a semipermeable membrane 18, and a closure cap 20. The microconcentrator device is adapted to fit, at least partially, within filtrate collection tube 12. In one embodiment, the various elements that make up the microconcentrator device may be conveniently disassembled and reassembled. This feature permits the microconcentrator device to be reused simply by disassembling the device, cleaning the various components, and reassembling the device while using a new membrane. Alternatively, the components of the microconcentrator device can be substantially permanently assembled such that it is not normally possible to disassemble the device.

The microconcentrator device of the invention may be used in well known ultrafiltration techniques to concentrate, separate and purify small volume samples of solutions and suspensions, such as proteins, viruses, and nucleic acids. The device can be used with ultrafiltration membranes having desired retention characteristics.

Among the advantages of the microconcentrator device of the invention is its reusability. This feature renders the device economical to use and thus significantly reduces costs in comparison to conventional disposable devices. Despite the ability of the microconcentrator device to be disassembled and reassembled, the device possesses suitable sealing properties such that separation and concentration techniques can be reliably performed with little or no risk that macro solute will seep from the sample sleeve to the filtrate collection tube. In addition., the microconcentrator device features an impermeable deadstop region which prevents filtration to dryness and ensures that a retentate volume in the range of 3–30 μL, and most preferably about 3–5 μL, will remain in the sample sleeve. The deadstop region is constructed such that it ensures that retentate will not be lost through leakage, for example.

As shown in FIG. 1, the microconcentrator device 10 includes an elongate sample sleeve 14 having centripetal and centrifugal ends 22, 24. When assembled for use, the sleeve is placed inside a filtrate collection tube 12, which is substantially conically shaped. A centripetal portion of sleeve 14, including centripetal end 23, protrudes from the open, centripetal end 26 of collection tube 12. A vented cap 20 seals the opening in the centripetal end 22 of the sample sleeve to prevent or minimize spillage and evaporation during or after filtration procedures.

FIGS. 2–5 further illustrate the microconcentrator device of the invention. The centrifugal end 24 of sleeve 14 includes an interior, annular ledge 28 which extends from the interior wall 30 of sleeve 14 and which has centripetal 39 and centrifugal 38 surfaces. Two or more legs or tabs 32 form a part of the centrifugal end 24 of sleeve 14 and extend below the ledge 28. The tabs 32 include surface features 34 that are able to engage the removable base element 16 to couple the base element 16 to the sleeve 14. In an embodiment illustrated in FIGS. 3A and 4, surface features 34 are in the form of a centripetal-facing shoulder 35. The base element 16 is coupled to the sleeve such that the semipermeable filtration membrane 18 is sandwiched between the centripetal surface 36 of base 16 and the centrifugal surface 38 of annular ledge 28. Preferably, a gasket or O-ring 40 may be mounted on the centripetal surface 36 of the base to abut the centrifugal surface 42 of the membrane 18.

Figures 3A, 3B:
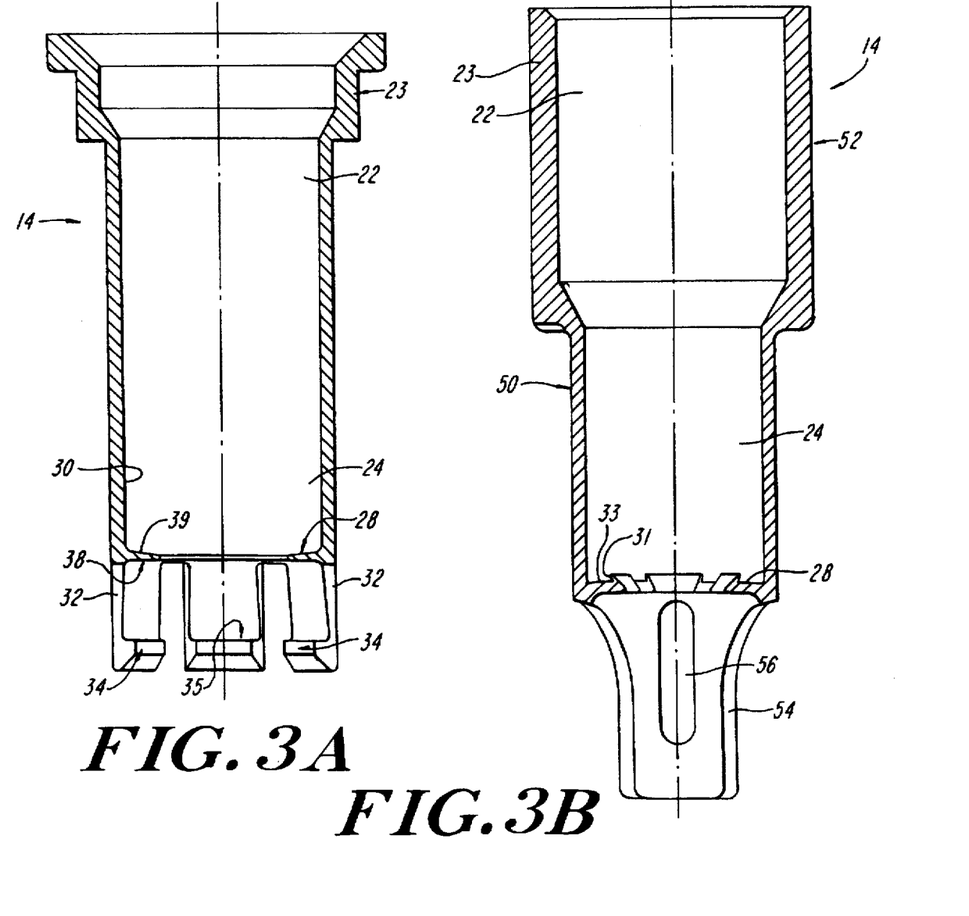
FIG. 3A is a sectional view of the sample receiving sleeve shown in FIG. 2, at lines 3—3.
FIG. 3B is a sectional view of an other alternative embodiment for the sample sleeve shown in FIG. 3A.

In one embodiment, as illustrated in FIG. 3A, the portion of the sleeve centripetal to the ledge 28 is of a substantially constant diameter along virtually all of its length. However, as illustrated, the diameter increases in one or more steps at the centripetal end 23 of the sleeve.

As illustrated in FIGS. 2–5, tabs 32 extend below annular ledge 28 to form the bottom-most portion of the sleeve. Preferably, the tabs 32 are somewhat compliant, permitting them to be flexed outwardly when subjected to a sufficient force. This force imparted to tabs 32 increases the inner diameter of that portion of the sleeve defined by the tabs to an extent sufficient to allow the base element 16 to be inserted within the space defined by the tabs 32. The tabs include one or more surface features, such as centripetal-facing shoulder 35, which engages the base 16 to couple it to the sleeve 14 once the tabs return to their natural position.

FIGS. 1, 3B, 5, 9 and 10 illustrate an alternative embodiment of the sample sleeve 14. As shown, the portion of the sleeve centripetal to the annular ledge 28 has a narrow diameter region 50 and a more centripetally disposed wider diameter region 52. At least two compliant extensions 54 (similar to tabs 32) extend from the region of the sleeve centrifugal to ledge 28. Extensions 54 include an aperture 56, which preferably is elongated in the axial direction.

The annular ledge 28 should be oriented such that in its normal position, when not subjected to any forces, the centripetal 39 and centrifugal 38 surfaces of ledge 28 are angled at between about 0° and 89° centripetal to a line drawn perpendicular to an interior wall 30 of the sleeve. More preferably these surfaces are angled at about 0° to 60°. These surfaces may also be angled up to about 15° below (centrifugal) to a line drawn perpendicular to an interior wall 30 of the sleeve. It is understood that the centripetal 39 and centrifugal 38 surfaces of the ledge 28 need not be disposed at the same angle. For example, FIG. 1 illustrates a design in which centrifugal surface 38 is oriented at about 45° while centripetal surface 39 is oriented at about 8°. The angles referred to herein, unless otherwise indicated, are understood to be centripetal to a line dram perpendicular to an inner wall 30 of the sleeve.

The inclined (e.g., approximately 45°) angle of the centrifugal surface 38 of ledge 28 is believed to provide an advantageous sealing compressive force to the centripetal surface of membrane 18.

In one embodiment, illustrated in FIG. 3B, ledge 28 includes a substantially vertically oriented annular lip 31. The lip 31 extends by approximately 0.005 to 0.02 inch above the base surface 33 of ledge 28. Lip 31 is useful in that it further ensures that retentate of a desired volume will remain within the sample sleeve, retained on ledge 28. As the angle of surface 39 becomes rather steeply inclined, lip 31 may be unnecessary.

Preferably, the sample sleeve is able to accommodate a volume of fluid 61 in the range of approximately 0.5 to 1.0 mL, and more preferably about 1.0 mL. These sleeves for the present device are adapted to fit within standard 1.9 mL microcentrifuge tubes, however a range of larger and smaller devices are intended to be covered by this invention to handle larger and smaller volumes in centrifuge rotors made for larger or smaller tubes.

By way of example, the diameter of the sleeve, in a region adapted to fit within the collection (microcentrifuge) tube 12 is in the range of approximately 0.28 to 0.35 inch. The diameter of a wider portion of the sleeve that does not fit within the collection tube is non-critical and can be in the range of about 0.35 to 0.50 inch. Typically the sleeve has a length, measured from the centripetal-most part of the sleeve to annular ledge 28, in the range of about 0.80 to 1.12 inch. The length of the tabs 32 and extensions 54 is typically about 0.15 to 0.30 inch. The annular ledge preferably extends toward the center of the sleeve by a distance of about 0.03 to 0.10 inch for devices designed to fit 1.9 mL microcentrifuge filtrate tubes.

As noted above, the collection tube 12 can be virtually any standard microcentrifuge tube. Preferably, the collection tube is a 1.9 mL microcentrifuge tube. Collection tube 12 is substantially conically shaped having a closed centrifugal end 58 and an open centripetal end 60. As illustrated in FIG. 1 sleeve 14 is positioned within the open end 60 of collection tube 12 in a secure, frictional fit. One of ordinary skill in the art will appreciate that surface features are normally present on the outer walls of the sleeve, or on the inner walls of the collection tube, to allow venting of the collection tube and also to facilitate easy removal of the sleeve from the collection tube. The surface features can be in the form of ridges, channels, protrusions, and the like.

The tabs 32 or extensions 54 disposed on the centrifugal end 24 of sleeve 14 can also serve as flexible, self-venting features of the sleeve. As noted above, tabs 32 and extensions 54 are somewhat compliant. That is, the tabs 32 or extensions 54 can be flexed outwardly to increase the inner diameter of the area defined by tabs 32 or extensions 54 in order to fit the base element 16 within this area. Once the base is properly positioned, the tabs 32 or extensions 54 return to their normal position to firmly engage base 16. The positioning of the centrifugal end 24 of sleeve 14 within a filtrate collection tube also forces tabs or protrusions 32, 54 to compress the side walls of the base 16. This ensures that the sleeve 14 will securely mate within a variety of filtrate collection tubes having mouths of varying inner diameters, and that the base will be securely mounted within the sleeve.

Figure 8:
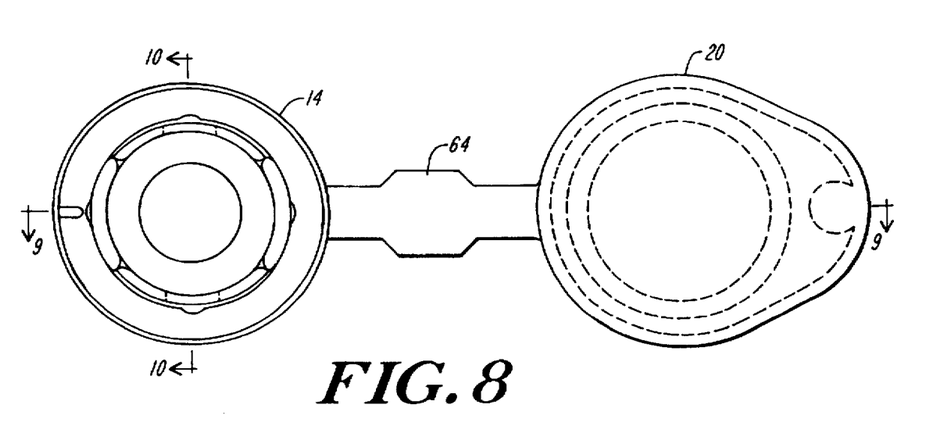
FIG. 8 is a bottom view of another embodiment of a sample receiving sleeve useful with the microconcentrator device of the invention.
Figures 9, 10:
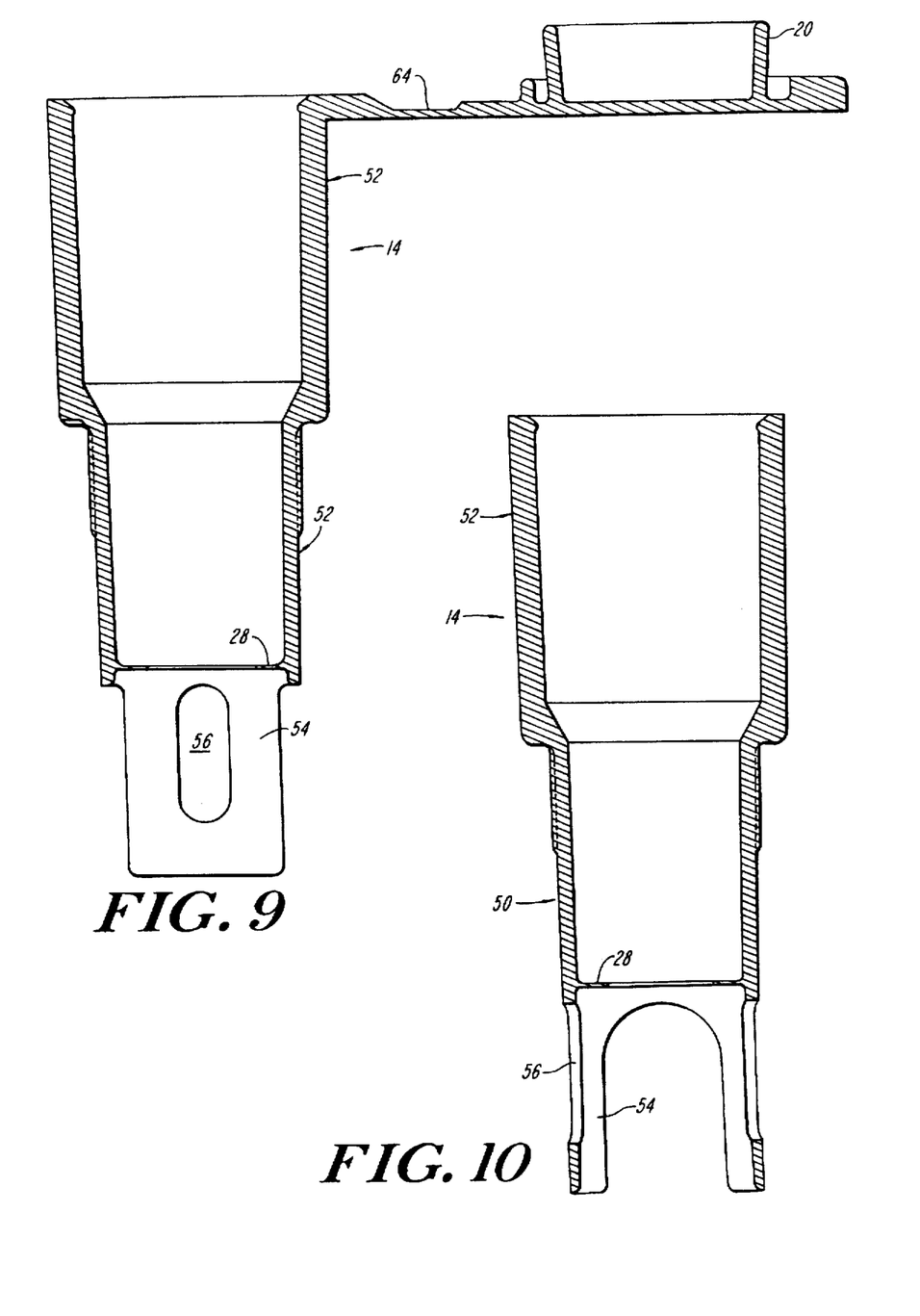
FIG. 9 is a side sectional view of the sample receiving sleeve shown in FIG. 8, at lines 9—9.
FIG. 10 is a front, sectional view of the sample receiving sleeve of FIG. 8, at lines 10—10.

A cap 20 is also provided to mate with the centripetal, open portion of the sleeve 14 to prevent spillage and/or evaporation of any fluid contents before, during or after centrifugation. As illustrated in FIGS. 8 and 9, the cap 20 may be attached by way of hinge 64 to a centripetal portion of the sleeve 14. This design is useful with respect to sleeves, such as those illustrated in FIGS. 3B, 9 and 10, which have a centripetal portion extending well above the open, top (centripetal) portion of the collection tube 12.

Base element 16 is adapted to be removably and replaceably coupled to a portion of the sleeve adjacent to and centrifugal to the annular ledge 28. Base 16 is a substantially disk-shaped object having a centripetal surface 36 and a centrifugal surface 37. One or more apertures 70 extend between the centrifugal and centripetal surfaces of the base element to provide flow conduits for filtrate. The base also includes one or more surface features 72 that interact with surface features 34 of tabs 32 and/or with apertures 56 of extensions 54 to permit coupling of the base to the sleeve.

Figure 4:
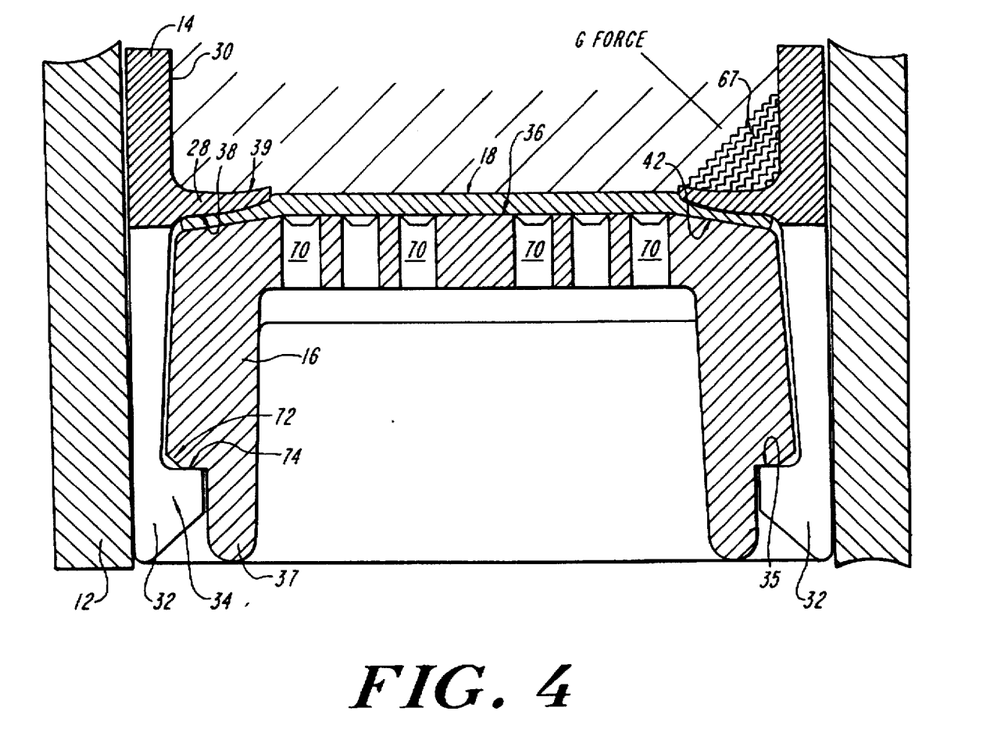
FIG. 4 is a side sectional view of the sample receiving sleeve of FIG. 3A coupled to a removable base.

In one embodiment, illustrated in FIG. 4, the surface feature 72 of base 16 is in the form of an annular, centrifugally-facing shoulder 74. As illustrated, a centrifugal-most portion of the base is of a slightly smaller outside diameter than is the remainder of the base, thus creating centrifugal-facing shoulder 74. Shoulder 74 is adapted to engage the complementary surface feature 34 of tabs 32. Shoulder 74 is approximately 0.015 to 0.03 inch in width.

Alternative surface features that can be formed on base 16 are illustrated in FIGS. 5 and 11-14. As illustrated, base 16 may have at least two outwardly flared protrusions 78 that fit within apertures 56 of the compliant extensions 54 formed in the sleeve of the type illustrated in FIGS. 1, 5, 9 and 10.

Figure 6:
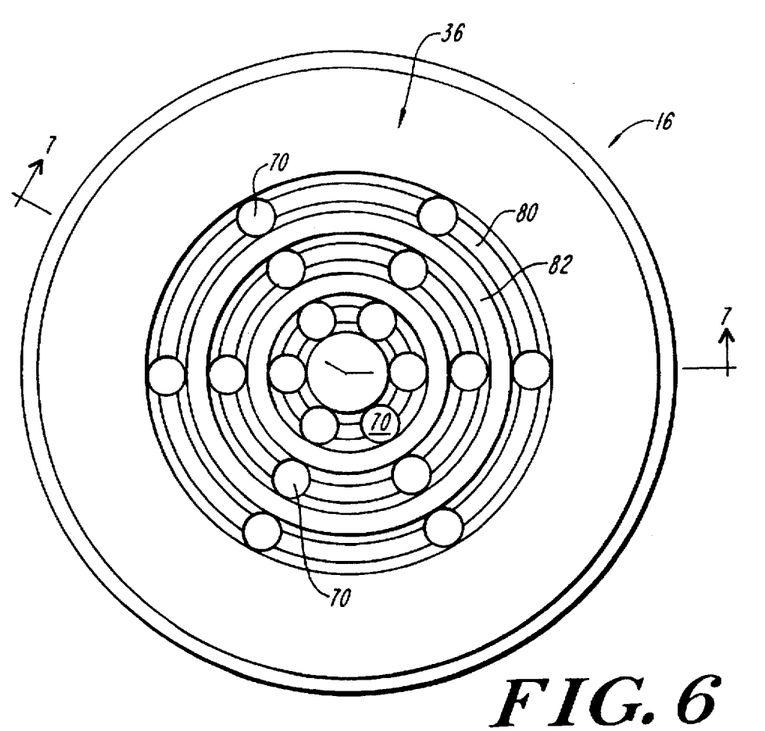
FIG. 6 is a top view of the removable base shown in FIG. 4, useful with the present invention.
Figure 7:
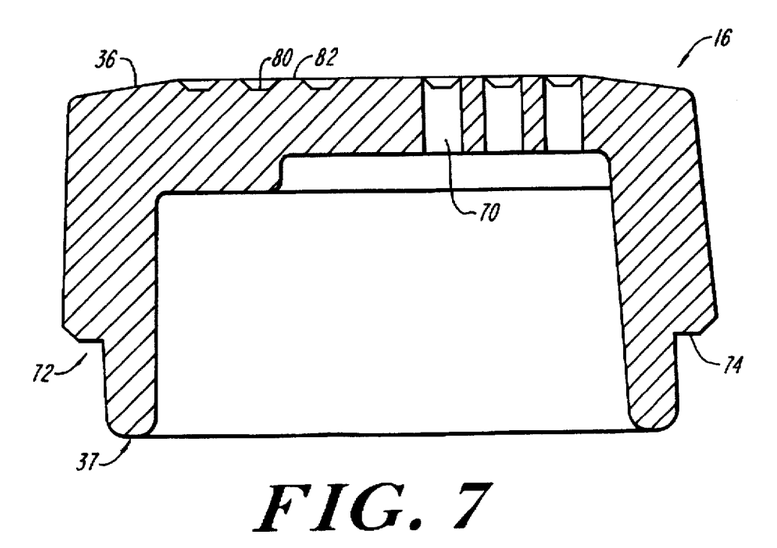
FIG. 7 is a sectional view of the base shown in FIG. 6, at lines 7—7.

The centripetal surface 36 of base 16 is designed to promote flow of filtrate to and through the apertures 70. Preferably, the centripetal surface 36 of the base is of a substantially convex cross section. As illustrated in FIGS. 6 and 7, the centripetal surface 36 may have a plurality of concentric grooves 80 that are separated by concentric raised ridges 82. One or more apertures 70 preferably is disposed within each of the grooves 80. Apertures 70 typically are of a small diameter in the range of about 0.01 to 0.02 inch.

Figure 11:
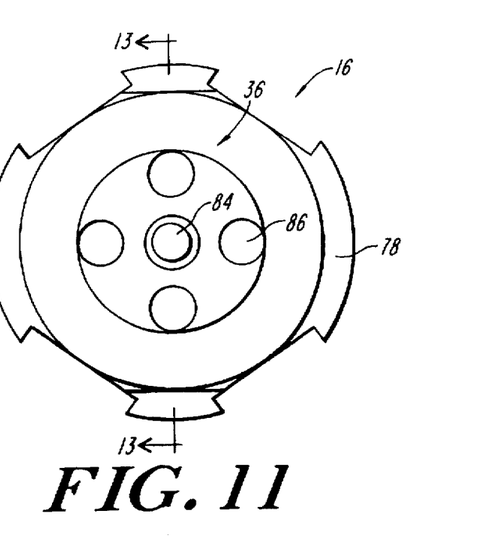
FIG. 11 is a top view of an alternative design for a removable base that is useful with the microconcentrator device of the present invention.
Figure 12:
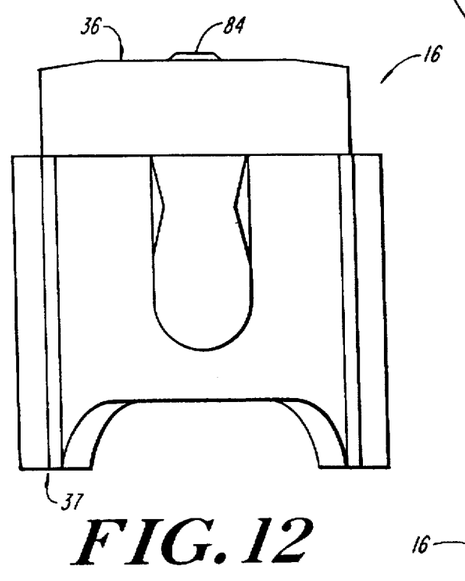
FIG. 12, is a side view of the base shown in FIG. 11.
Figure 13:
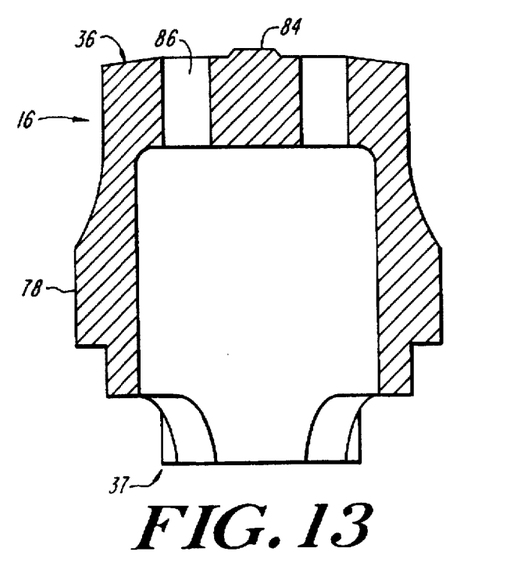
FIG. 13 is a sectional view at lines 13-13 of the base shown in FIG. 11.

Alternatively, as illustrated in FIGS. 11-13, the centripetal surface 36 of base 16 may include a central raised ridge 84 and have one or more apertures 86 disposed radially outward from the ridge 84. Apertures 86 generally are of a diameter somewhat larger than apertures 70, thus making it possible to use fewer apertures. Apertures 86 have a diameter in the range of about 0.025 to 0.06 inch.

Figure 14:
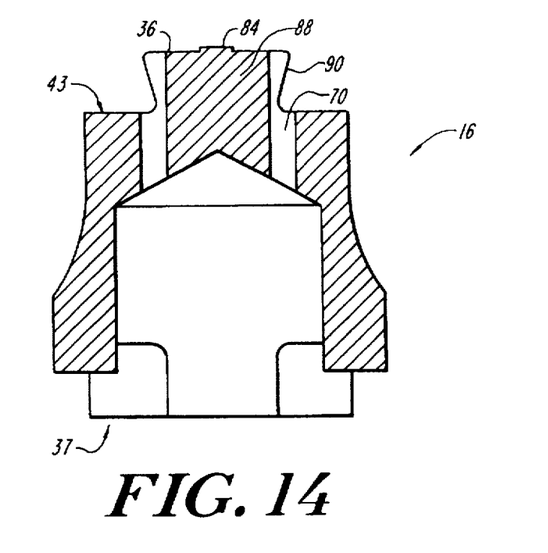
FIG. 14 is a side, sectional view of the design for a removable base shown in FIG. 1 that is useful with the microconcentrator device of the present invention.

FIG. 14 illustrates another embodiment of base 16 that is specifically adapted to house an O-ring 40. In this embodiment; base 16 includes a tapered, annular spool 88 formed adjacent (and centripetal to) intermediate surface 43. An O-ring (not shown) is mounted around spool 88 such that a bottom (centrifugal) surface of the O-ring abuts intermediate surface 43 of base 16. One or more filtrate flow ducts 90 are formed in the centripetal surface 36 adjacent the tapered annular spool 88, extending up the tapered annular walls of spool 88 as grooves to conduct filtrate past the inner surface of the O-ring.

The membrane useful with the present invention can be virtually any semipermeable anisotropic (skinned) ultrafiltration membrane. Suitable membrane materials include polysulfone, polyether sulfone, cellulose esters, and regenerated cellulose polymers. Exemplary commercially available membranes include the MILIPORE BIOMAX, the AMICON YM and the FILTRON OMEGA. Obviously, the filtration device of the invention is intended to accept membranes having a variety of desired molecular weight cutoffs and other properties useful in filtration and separation.

One of ordinary skill in the art can readily determine a membrane diameter suitable for use with a microconcentrator device of the present invention. Generally, the membrane should have a diameter that, on the large end, is at least about equal to or slightly greater than the inside diameter of the sample sleeve. On the small end, the membrane diameter can be slightly greater than the diameter of the flow path defined by the annular ledge 28 plus the width of one side of the annular ledge 28, thereby ensuring that even with maximal misalignment of the membrane and device axes during assembly there will not be a void space in which ledge 28 fails to crush and seal the membrane. In a preferred embodiment the membrane diameter is approximately 9/32 inch. The membrane should be of sufficient thickness to be crushable between the base and the annular flange in order to create a sufficient seal and to prevent leakage of unfiltered sample into the filtrate collection tube. Generally, the membrane thickness is in the range of 0.008 to 0.012 inch.

As noted above, the microconcentrator device of the invention is reusable. As a reusable device, it must be able to be easily disassembled to facilitate cleaning, and then easily reassembled. The device may be assembled for use as follows, with reference to FIG. 1, unless otherwise noted.

The sleeve 14 is most conveniently inverted upon a work surface, and a suitable ultrafiltration membrane 18 is placed on the centrifugal surface 38 of the ledge 28, with its skin side facing down, in the centripetal direction. The base 16 is then pushed down into the sleeve by hand, or with a suitable insertion tool.

In one embodiment, illustrated in FIG. 4, the shoulders 35 of tabs 32 engage the shoulders 74 of the base 16. This engagement imparts a force on the base 16 which causes membrane 18 to be securely held between the centripetal surface 36 of the base 16 and the centrifugal surface 38 of the ledge 28. This engagement provides a suitable seal between the membrane, base and the ledge to prevent any leakage of any unfiltered sample. In one embodiment, the coupling force imparted upon the base also causes the ledge 28 to deflect and to flex upwardly (in the centripetal direction) up to an additional 30°, creating a stress in the sleeve ledge 28 and wall which serves to maintain the crushing seal between ledge 28 and the membrane skin.

Figure 5:
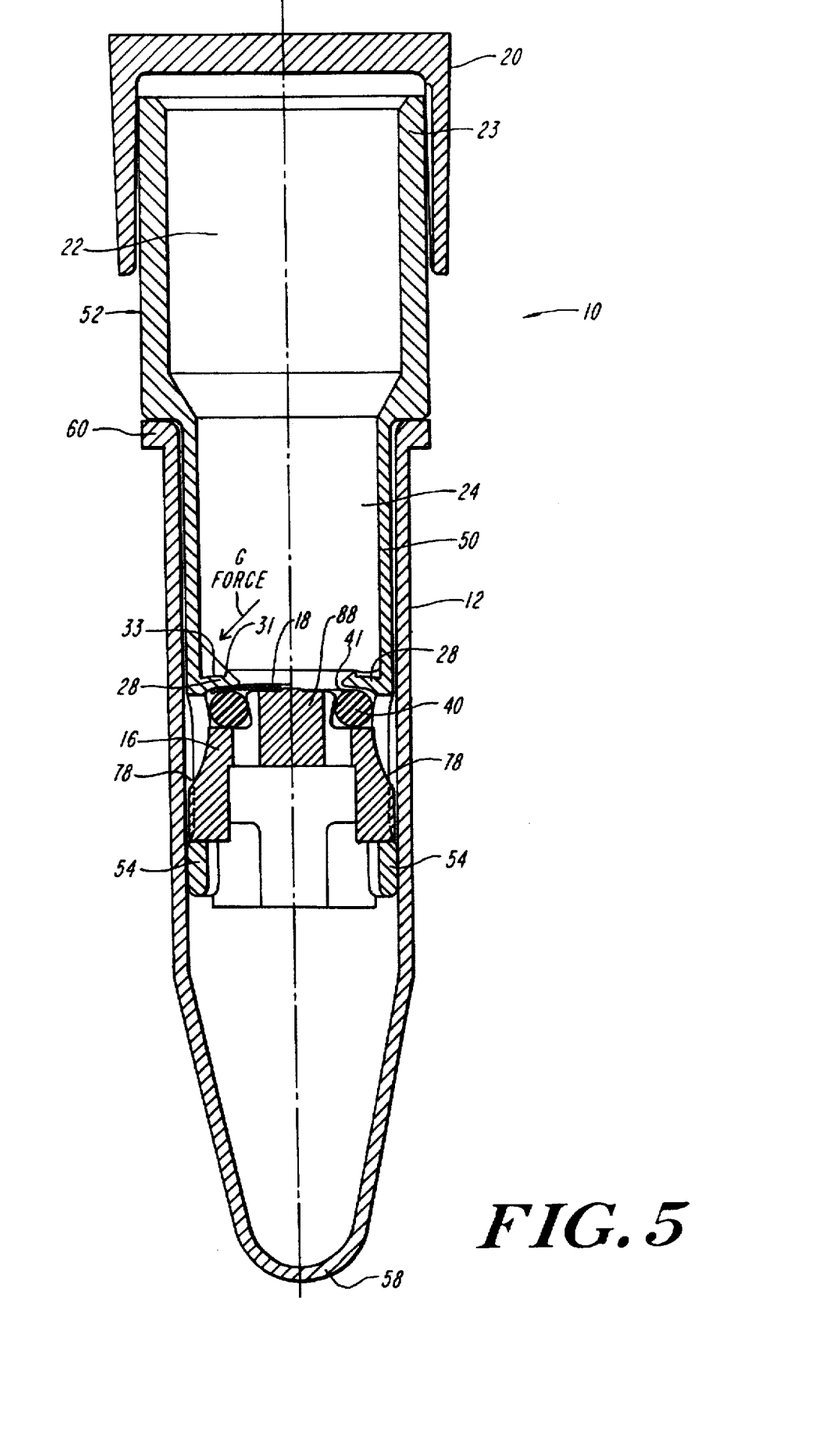
FIG. 5 is a side sectional view of the sample sleeve shown in FIG. 3B, coupled to the base and disposed within the filtrate collection tube.

As illustrated in FIG. 5, O-ring 40, when desired for use, may be placed beneath (centrifugal to) the membrane 18 to energize the sealing crush of the membrane against ledge 28. The O-ring 40 may be positioned on the centripetal surface 36 of the base such that it engages the centrifugal side 42 of the membrane. Although not illustrated, the O-ring may also be used to augment the seal shown in the embodiment illustrated in FIG. 4. FIG. 5 illustrates the use of a base 16 which includes a tapered annular spool 88 that houses O-ring 40. As shown, the membrane 18 mounts atop the centripetal surface 36 of base 16 and the centripetal surface 41 of O-ring 40.

The O-ring preferably is a ring-shaped object that has an outside diameter sufficient to compress the membrane 18 against the centrifugal surface 38 of ledge 28. The inside diameter of the O-ring should be such that it fits around spool 88, without falling off, when the device is disassembled. Preferably the relaxed outside diameter of the O-ring is about 0.25 inch and the inside diameter of the O-ring is approximately 0.125 inch, as in a standard commercial ring size 2-006. The O-ring has a thickness of about 0.03 to 0.08 inch, and preferably a thickness of about 0.07 inch. The O-ring can be made of virtually any elastomeric material. A preferred material is an ethylene propylene (EPR or EPDM).

The device design shown in FIGS. 1 and 14 has the advantage of a dramatic increase in available filtration surface area and resulting filtration rate due to the use of a steeply angled (45 degree) centrifugal surface 38 of ledge 28. This design fits a standard 1.9 mL microcentrifuge tube. When tested at 12,000 rcf using a commercial polysulfone 10 kD membrane it has been found to concentrate 1 mL (maximal capacity) of 0.1% Blue Dextran down to a deadstop volume 67 of 4 µL in less than 30 minutes without visible leakage. The initial 2× volume reduction was accomplished in 5 minutes, due to the 214 psi initial transmembrane pressure generated by the 0.5 inch meniscus height of 1 mL in this design mounted in a 45 degree microcentrifuge at 12,000 rcf. The 45 degree centrifugal ledge surface angle (centripetal to a line drawn perpendicular to a wall of the sleeve) design achieves an active filtration surface area of 0.0506 in$^2$.

By contrast, a design with a 16 degree ledge surface angle (centripetal to a line drawn perpendicular to a wall of the sleeve) having equivalent initial and deadstop ledge volume has an active surface area of only 0.0278 in$^2$. This is due in part to the larger inner diameter of a ledge having a centrifugal surface disposed at a 45 degree angle, made possible, for the given 4 µL deadstop volume, by the downward angle of the centripetal surface of ledge 28, which results in a 1.28 fold increase in active area over the ledge design in which the centrifugal surface of the ledge is disposed at 16 degree angle. The fact that the membrane is able to be formed into a smoothly curved dome shape by spool 88, O-ring 40, and ledge surface 38, when the centrifugal ledge surface is disposed at 45 degrees, results in a further 1.55 fold increase in active area over the equivalent diameter flat membrane. The overall result is a 1.98 fold increase in active filtration area.

Once assembled the microconcentrator device 10 of the invention can be used in a typical manner. Following filtration, the ledge enables a reliable volume of retentate 67, approximately 3 to 30 µL, and more preferably about 3–5 µL, to remain in the sample sleeve 14, thus preventing filtering to dryness.

After use disposable versions of the device can be disassembled and the membrane can typically be removed and discarded. The various components of the microconcentrator device may be cleaned, such as with a detergent solution, and reused. Those of ordinary skill in the art will appreciate that the microconcentrator device of the invention can be manufactured in disposable versions as well in which the various elements of the device are substantially assembled.

Figure 15:
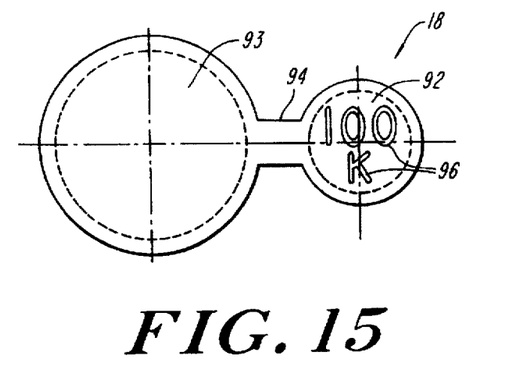
FIG. 15 is a top view of one embodiment of a filtration membrane useful with the present invention.
Figure 16:
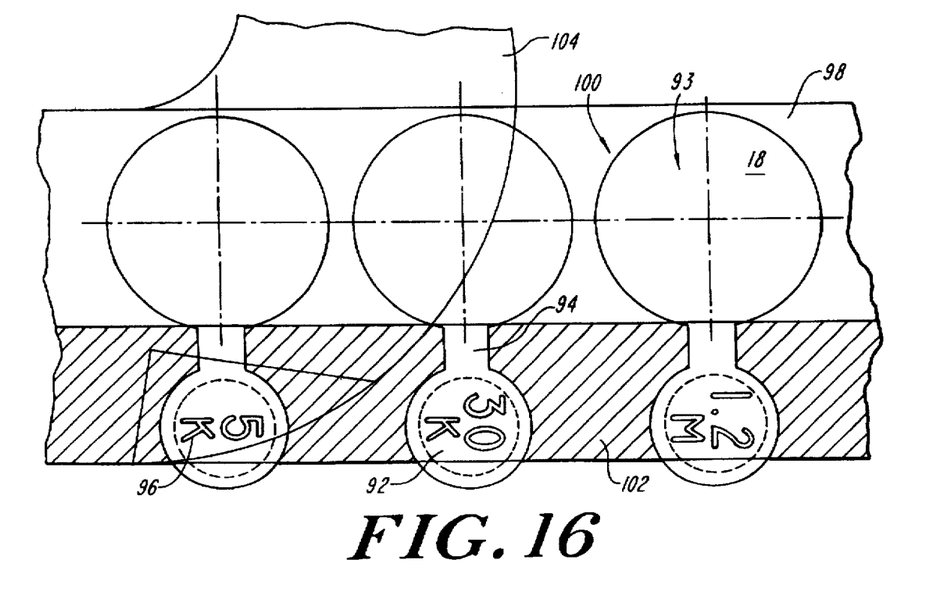
FIG. 16 is a top view, partially cut away, of a filtration membrane dispensing system useful with the present invention.

FIGS. 15 and 16 illustrate convenient designs for filtration membranes and a filtration membrane dispensing system useful with the microconcentrator device of the invention.

As illustrated (FIG. 15), membrane 18 includes a non-filtering handling tab 92 which is appended to a filtering portion 93 of membrane 18 by bridge 94. Preferably, the filtering portion, tab and bridge are integrally formed. The tab serves a useful function in that it promotes easy handling of the filtering portion of the membrane for positioning the membrane within a microconcentrator device and for removing the membrane from a microconcentrator device. This feature allows the membrane to be easily and conveniently handled and manipulated without contacting or contaminating the sensitive skin surface of the membrane. The tab can be of a variety of useful shapes, such as substantially circular or rectangular.

The tab may also be used as a surface upon which to affix indicia 96 concerning membrane properties such as molecular weight cutoff. Indicia may be affixed to the tab with, for example, a heated die to discolor the tab with an image representing the desired information concerning membrane properties. Indicia 96 may also be formed on the tabs 92 by printing techniques. Preferably, it has been found that indicia 96 may be formed simply by die stamping an impression which compresses the tab and substructure to cause the affected portions of the tab to become transparent.

Generally, the size of tab 92 is non-critical and suitable dimensions can be determined by one of ordinary skill in the art. In preferred embodiments the tab and bridge are combined into a rectangular shape which is about 0.125 inch wide by 0.4 inch long.

In one embodiment, illustrated in FIG. 16, a plurality of membrane-tab units can be affixed to a dispenser strip 98. Preferably the filtering portion 93 of the membrane lies on a non-adhesive portion 100 of the dispenser strip 98. The tab and bridge elements 92, 94 may be disposed on an adhesive portion 102 of the dispenser strip. In addition, a protective release strip 104 may be disposed over the dispenser strip so as to cover the membranes, bridges and tabs. In many cases the adhesive present on the dispenser strip is sufficient to maintain the release strip 104 in place. Alternatively, adhesive may be applied to cover all or part of the dispenser strip- and membrane-contacting surface of the release strip 104. Adhesives suitable for this purpose include repositionable and transfer silicones and acrylics, which are well known in the art. Suitable examples include the Drybonder™ instant tack repositionable transfer adhesive system manufactured by Chartpak, and Post-it™ 658 correction and cover-up tape and Scotch® brand 2070 SAFE RELEASE masking repositionable tapes both manufactured by 3M.

Once assembled in this manner the membranes, dispenser strip and release strip may be perforated to facilitate removal of waste tape after use, and collected on a reel or spool for easy handling and dispensing.

The following non-limiting examples serve to further illustrate the invention.

EXAMPLES

Membrane and device flux comparisons were performed using a 0.1 g/dL solution of Blue Dextran in distilled water. This solute, obtained from Sigma Chemical Company, has an average molecular weight of 2,000,000 daltons, and is made visible by incorporation of 0.1 mmol Reactive Blue dye/g dextran. A 0.001 g/dL solution was clearly visible by eye, permitting convenient confirmation of >99% membrane retention and seal integrity by visual inspection of filtrates.

EXAMPLE 1

Figure 17:
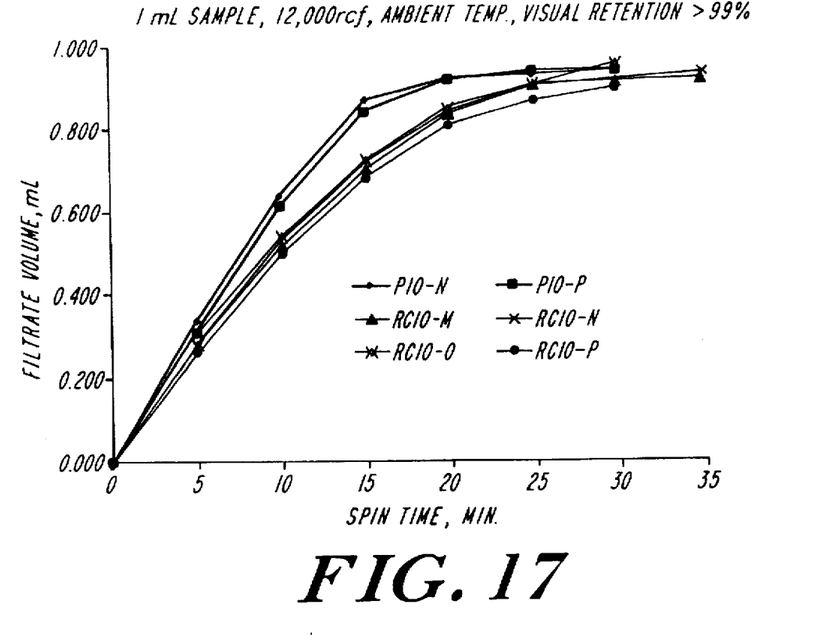
FIG. 17 is a graph illustrating the results of Example 1.

FIG. 17 is a comparison of microconcentrator devices according to the design of FIG. 1, having a 45 degree membrane sealing ledge (centrifugal surface of annular ledge). Modified polysulfone 10,000 dalton cutoff ultrafiltration membranes (here designated as P10) and regenerated cellulose 10,000 dalton cutoff ultrafiltration membranes (here designated as RC10) were tested with 1 mL starting volumes in an Eppendorf 5412 microcentrifuge. The 1.9 mL filtrate tubes were initially weighed, and weighed following each successive 5 min spin. Filtration rate is faster for 0.1% Blue Dextran with the P10 membrane, with maximal concentration seen in about 25 min. The RC10 regenerated cellulose membrane, known to be less porous, took an additional 10 min to reach maximal concentration.

EXAMPLE 2

Figure 18:
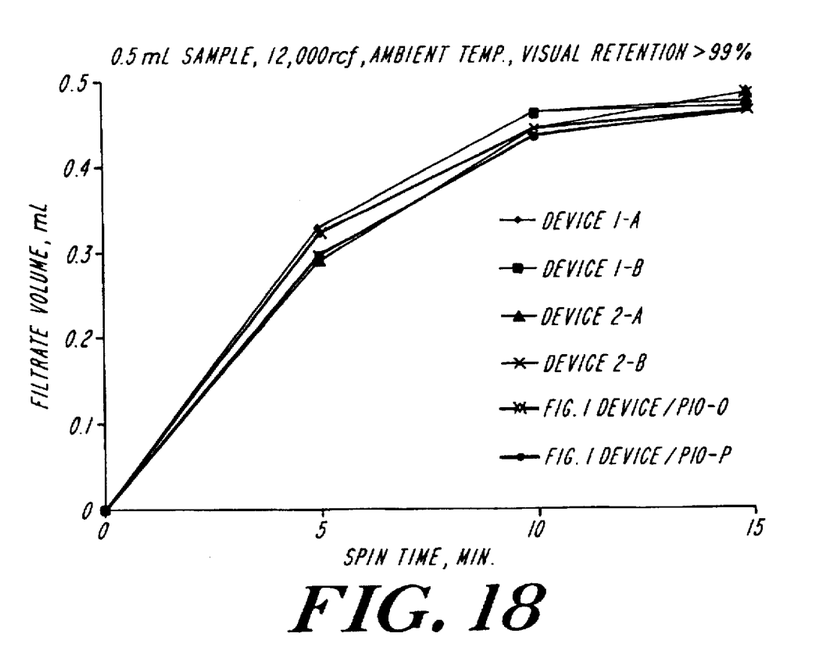
FIG. 18 is a graph illustrating the results of Example 2.

FIG. 18 is a similar study of the microconcentrator device of FIG. 1 using the P10 membranes compared to two commercially available disposable microconcentrator devices. Comparative Device 1 has an impermeable deadstop and a large surface area vertically-mounted P10 membrane. Comparative Device 2 is a deadstop-free, high filtration rate P10 microconcentrator. All devices were tested with 0.5 mL starting volume, and filtrate weights were again measured successively. As seen in Example 1, the flux curves for the FIG. 1 devices again required 15 min to go from 0.5 mL down to about 30 µL. In this study, all devices tested reached equivalent retentate volumes below 40 µL in 15 min, with no visual leakage.

The invention being thus disclosed, other variations and modifications, as well as adaptations to known microconcentrator devices will occur to those having ordinary skill in the art. All such variations, modifications and adaptations are within the spirit and scope of the invention as defined in the claims appended hereto.

The entirety of all references noted herein are expressly incorporated by reference.

What is claimed is:

1. A centrifugal filtration apparatus for separating and concentrating macromolecules or particles from a solution or a suspension, comprising:

an elongate sleeve adapted to mate with a filtrate collection tube, the sleeve being of a substantially cylindrical shape and having openings at centripetal and centrifugal ends thereof, the elongate sleeve further including a fluid retaining annular ledge disposed at a centrifugal portion of the sleeve;

a base element, removably and replaceably mountable upon the centrifugal end of the sleeve, the base element having a centripetal surface and a centrifugal surface with one or more apertures extending therethrough;

a coupling means for removably and replaceably mounting the base element to the centrifugal portion of the sleeve such that the base element is joined to the sleeve in a position centrifugal with respect to the annular ledge; and a semipermeable membrane removably mountable within the filtration apparatus such that it is maintained in position between the annular ledge and the centripetal surface of the base element.

2. The apparatus of claim 1 further comprising an O-ring member that abuts a peripheral portion of the base element and which is disposed between the base element and a centrifugal surface of the membrane.

3. The apparatus of claim 2 wherein the opening in the centripetal end of the elongate sleeve has a diameter greater than the opening in the centrifugal end of the elongate sleeve.

4. The apparatus of claim 2 wherein the O-ring element is disposed within an annular channel formed in the centripetal surface of the base element.

5. The apparatus of claim 1 further comprising a filtrate collection tube having a closed centrifugal end and an open centripetal end, wherein the distal end of the filtrate collection tube is conically shaped.

6. The apparatus of claim 1 wherein the centripetal surface of the base element has a plurality of concentric raised circular ridge segments.

7. The apparatus of claim 4 wherein the apertures are disposed between the concentric circular ridge segments.

8. The apparatus of claim 1 wherein the centripetal surface of the base element has a convex cross section.

9. The apparatus of claim 8 wherein the centripetal surface of the base element has one or more annular flow channels formed by one or more stepped shoulders.

10. The apparatus of claim 1 wherein the base element further includes one or more shoulders defined in an outer surface thereof.

11. The apparatus of claim 10 wherein the coupling means comprises two or more tab elements that extend centrifugally from a portion of the elongate sleeve adjacent to the annular ledge, each tab element having a surface feature that matingly engages a corresponding surface feature of the base element.

12. The apparatus of claim 11 wherein the tab elements are resilient and are able to be compressed upon insertion of the sleeve into a filtrate collection tube such that the force exerted upon an inner side wall of the filtrate collection tube by the compressed tab elements maintains contact between the sleeve and the filtrate collection tube.

13. The apparatus of claim 1 wherein the annular ledge is of sufficient resiliency such that it is able to deflect upwardly when subjected to a force applied by the base element when the base element is coupled to the elongate sleeve, thus providing a seal to the semipermeable membrane.

14. The apparatus of claim 1 wherein the annular ledge provides a reliable deadstop which retains a volume of retentate within the elongate sleeve in the range of about 3 to 30 µL.

15. The apparatus of claim 1 wherein the annular ledge extends inwardly from an inner wall of the elongate sleeve by approximately 0.03 to 0.1 inch.

16. The apparatus of claim 1 wherein the apertures have a diameter in the range of about 0.01 to 0.06.

17. The apparatus of claim 1 wherein the annular ledge includes an annular vertically extending lip appended to an interior edge of the ledge.

18. The apparatus of claim 17 wherein the annular vertically extending lip has a height in the range of 0.005 to 0.02 inch.

19. The apparatus of claim 1 wherein the annular ledge has a centrifugal surface disposed at an angle with respect to a normal to an interior wall of the sleeve and the centripetal surface of the base element has a convex shape, causing the centripetal surface of the semipermeable membrane to assume a convex shape having an increased surface area.

20. The apparatus of claim 19 wherein the angle defined by the centrifugal surface of the annular ledge and a line perpendicular to an interior wall of the sleeve centrifugal to the ledge is between about 5 and 89 degrees.

21. The apparatus of claim 19 wherein the base element includes an O-ring which assists in shaping the semipermeable membrane into a convex shape when the semipermeable membrane is engagingly sealed against the centrifugal surface of the annular ledge.

22. The apparatus of claim 1 wherein the semipermeable membrane has an extended tab means attached thereto for facilitating placement and removal of the membrane between the annular flange and the base element.

23. The apparatus of claim 22 wherein the tab means includes indicia identifying pore size, molecular weight cutoff rating, and/or the active skin side of the membrane.

24. A centrifugal filtration apparatus for separating and concentrating macromolecules or particles from a solution or a suspension, comprising:

an elongate sleeve adapted to mate with a filtrate collection tube, the sleeve being of a substantially cylindrical shape having openings at centripetal and centrifugal ends thereof, the elongate sleeve further including an annular ledge disposed at a centrifugal portion of the sleeve, the annular ledge having an angled centrifugal surface;

a base element, mounted upon a centrifugal end of the sleeve, the base element having a centripetal surface and a centrifugal surface with one or more apertures extending therethrough, the centripetal surface being convexly shaped thereby causing the centripetal surface of the semipermeable membrane to assume a convex shape having an increased surface area;

a coupling means for mounting the base element to a centrifugal portion of the sleeve such that the base element is joined to the sleeve centrifugal to the annular ledge;

a semipermeable membrane mounted within the filtration apparatus such that it is maintained in position between the annular ledge and the centripetal surface of the base element; and a compliant compressing means for crushing and sealing the centripetal surface of the semipermeable membrane to the centrifugal surface of the annular ledge.

25. The apparatus of claim 24 in which the compliant compressing means is an O-ring member that abuts a peripheral portion of the base element and which is disposed between the base element and the membrane to provide a compliant compressing membrane seal.

26. The apparatus of claim 24 in which the compliant compressing means is a compliant annular ledge which possesses sufficient flexibility to provide a compliant compressing membrane seal.

27. The apparatus of claim 24 wherein the angle defined by the centrifugal surface of the annular ledge and a line perpendicular to an interior wall of the sleeve centrifugal to the ledge is between about 5 and 89 degrees.

28. The apparatus of claim 24 wherein the base element includes an O-ring which assists in shaping the semipermeable membrane into a convex shape when the semipermeable membrane is engagingly sealed against the centrifugal surface of the annular ledge.

29. A centrifugal apparatus for separating and concentrating macromolecules or particles from a solution or suspension comprising:

an elongate sleeve adapted to mate with a filtrate collection tube, the sleeve being of a substantially cylindrical shape, having openings at centripetal and centrifugal ends thereof, the elongate sleeve further including an annular ledge, disposed at a centrifugal portion of the sleeve, which has a centrifugal surface angled between about 5 and 89 degrees centripetal to a line drawn perpendicular to the interior wall of the sleeve;

a base element mounted upon a centrifugal end of the sleeve, the base element having a substantially convex shaped centripetal surface, and a centrifugal surface with one or more apertures extending therethrough;

a coupling means for mounting the base element to a centrifugal portion of the sleeve such that the base element is joined to the sleeve centrifugal to the annular ledge; and a semipermeable membrane mounted within the filtration apparatus such that it is maintained in a substantially convex shape in a position between the annular ledge and the centripetal portion of the base element.

\* \* \* \* \*